(12) United States Patent
Burgess et al.

(10) Patent No.: US 9,974,878 B1
(45) Date of Patent: May 22, 2018

(54) SCENT-DISPENSING ANIMAL COLLAR ACCESSORY

(71) Applicant: Michael Burgess, Jersey City, NJ (US)

(72) Inventors: Michael Burgess, Jersey City, NJ (US); Barbara Burgess, Jersey City, NJ (US)

( * ) Notice: Subject to any disclaimer, the term of this patent is extended or adjusted under 35 U.S.C. 154(b) by 150 days.

(21) Appl. No.: 15/156,521

(22) Filed: May 17, 2016

(51) Int. Cl.
| | |
|---|---|
| *A61L 9/00* | (2006.01) |
| *A61L 9/013* | (2006.01) |
| *A01K 27/00* | (2006.01) |
| *A61L 9/012* | (2006.01) |

(52) U.S. Cl.
CPC .............. *A61L 9/00* (2013.01); *A01K 27/008* (2013.01); *A61L 9/012* (2013.01); *A61L 9/013* (2013.01); *A61L 2209/13* (2013.01)

(58) Field of Classification Search
CPC ......... A61L 9/00; A61L 9/013; A01K 27/007; A01K 27/008
USPC ....................................................... 422/123
See application file for complete search history.

(56) References Cited

U.S. PATENT DOCUMENTS

| | | |
|---|---|---|
| 2,808,030 A | 10/1957 | Costanzo |
| 4,068,624 A | 1/1978 | Ramney |
| 4,208,986 A | 6/1980 | Costanzo |
| 6,101,981 A | 8/2000 | Friend |
| D444,599 S | 7/2001 | Guerry, Jr. |
| 7,185,613 B2 | 3/2007 | Arvanitis |
| D605,276 S | 12/2009 | Beardmore |
| 2011/0120392 A1 | 5/2011 | Smith |
| 2015/0250166 A1* | 9/2015 | Goldblum .............. A01N 35/06 424/45 |
| 2015/0335104 A1* | 11/2015 | Dickie ................... A44B 13/02 119/792 |

* cited by examiner

*Primary Examiner* — Kevin Joyner
(74) *Attorney, Agent, or Firm* — Kyle A. Fletcher, Esq.

(57) ABSTRACT

The scent-dispensing animal collar accessory is adapted for use with a collar that is worn by an animal. The scent-dispensing animal collar accessory is a container that is attached to the collar. The container is used to contain a fragrance device. The fragrance device is a chemical device that releases one or more aroma compounds. Air flow through the container will disperse the one or more aroma compounds into the atmosphere in a manner that deemphasizes existing aromas that may be associated with the animal. The scent-dispensing animal collar comprises a container, an attachment device, and a fragrance device.

9 Claims, 3 Drawing Sheets

US 9,974,878 B1

SCENT-DISPENSING ANIMAL COLLAR ACCESSORY

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of methods and apparatus of sterilizing materials or objects, more specifically, an apparatus for the deodorizing of air.

SUMMARY OF INVENTION

The scent-dispensing animal collar accessory is adapted for use with a collar that is worn by an animal. The scent-dispensing animal collar accessory is a container that is attached to the collar. The container is used to contain a fragrance device. The fragrance device is a chemical device that releases one or more aroma compounds. Air flow through the container will disperse the one or more aroma compounds into the atmosphere in a manner that deemphasizes existing aromas that may be associated with the animal.

These together with additional objects, features and advantages of the scent-dispensing animal collar accessory will be readily apparent to those of ordinary skill in the art upon reading the following detailed description of the presently preferred, but nonetheless illustrative, embodiments when taken in conjunction with the accompanying drawings.

In this respect, before explaining the current embodiments of the scent-dispensing animal collar accessory in detail, it is to be understood that the scent-dispensing animal collar accessory is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the scent-dispensing animal collar accessory.

It is therefore important that the claims be regarded as including such equivalent construction insofar as they do not depart from the spirit and scope of the scent-dispensing animal collar accessory. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
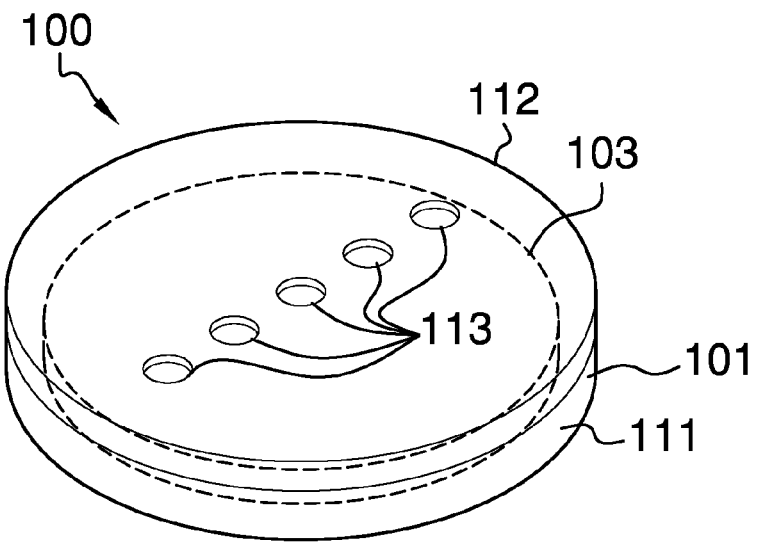
FIG. 1 is a perspective view of an embodiment of the disclosure.
Figure 2:
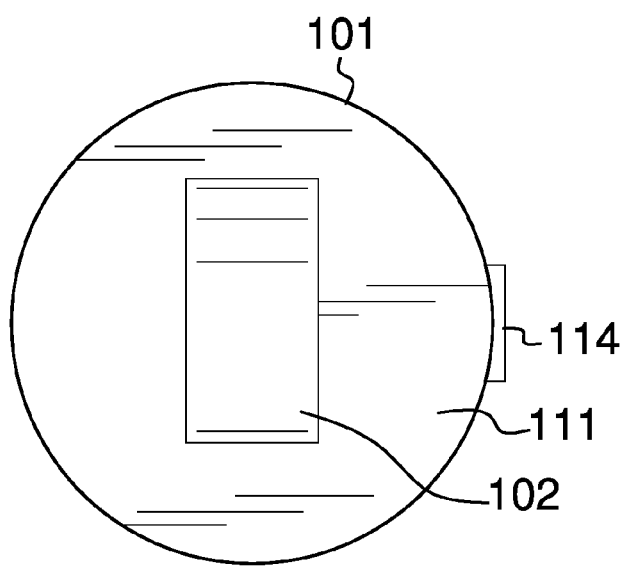
FIG. 2 is a bottom view of an embodiment of the disclosure.
Figure 3:
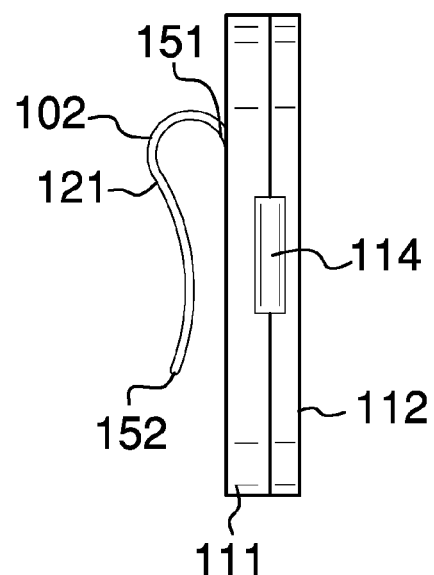
FIG. 3 is a side view of an embodiment of the disclosure.
Figure 4:
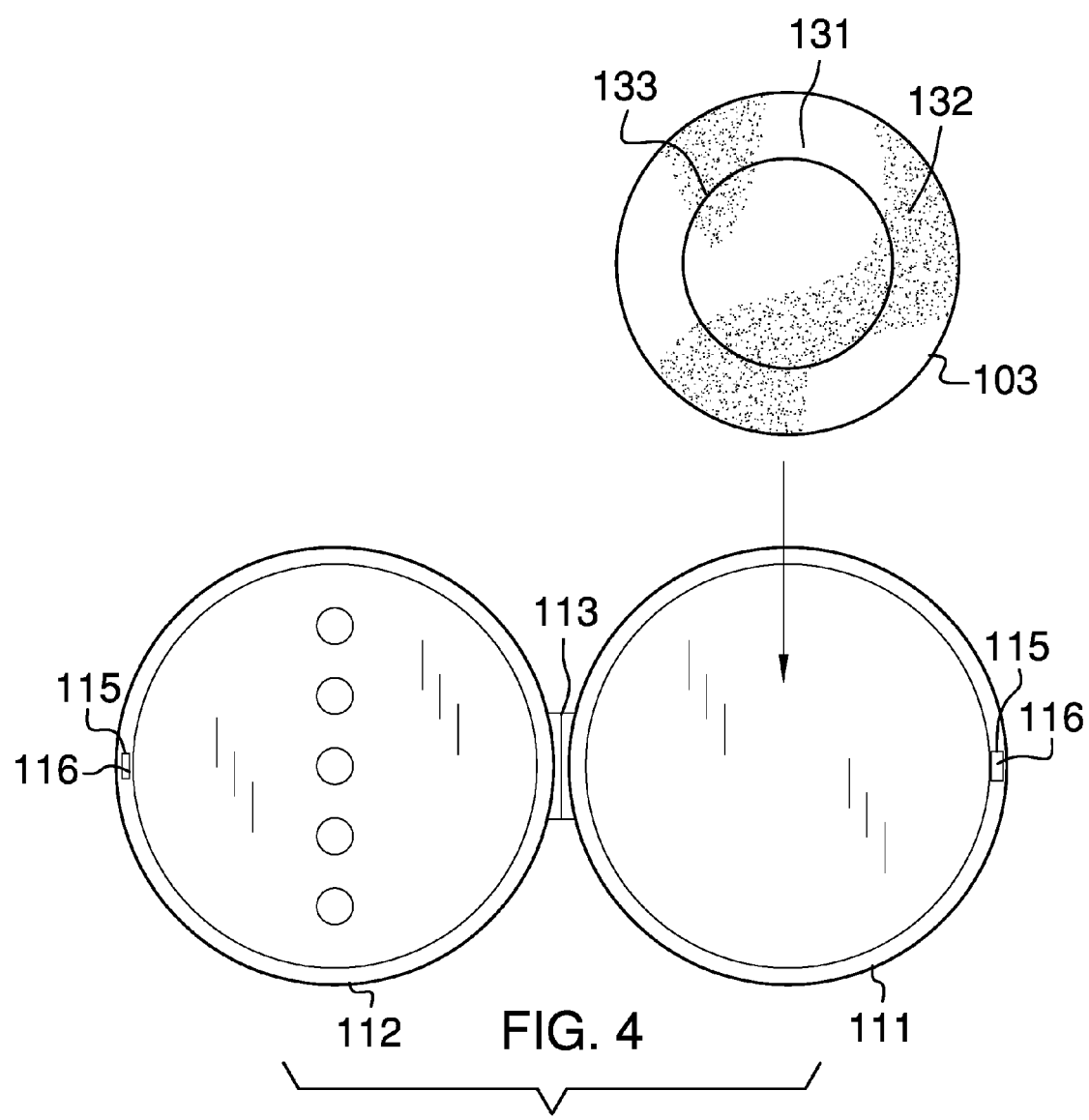
FIG. 4 is an open view of an embodiment of the disclosure.
Figure 5:
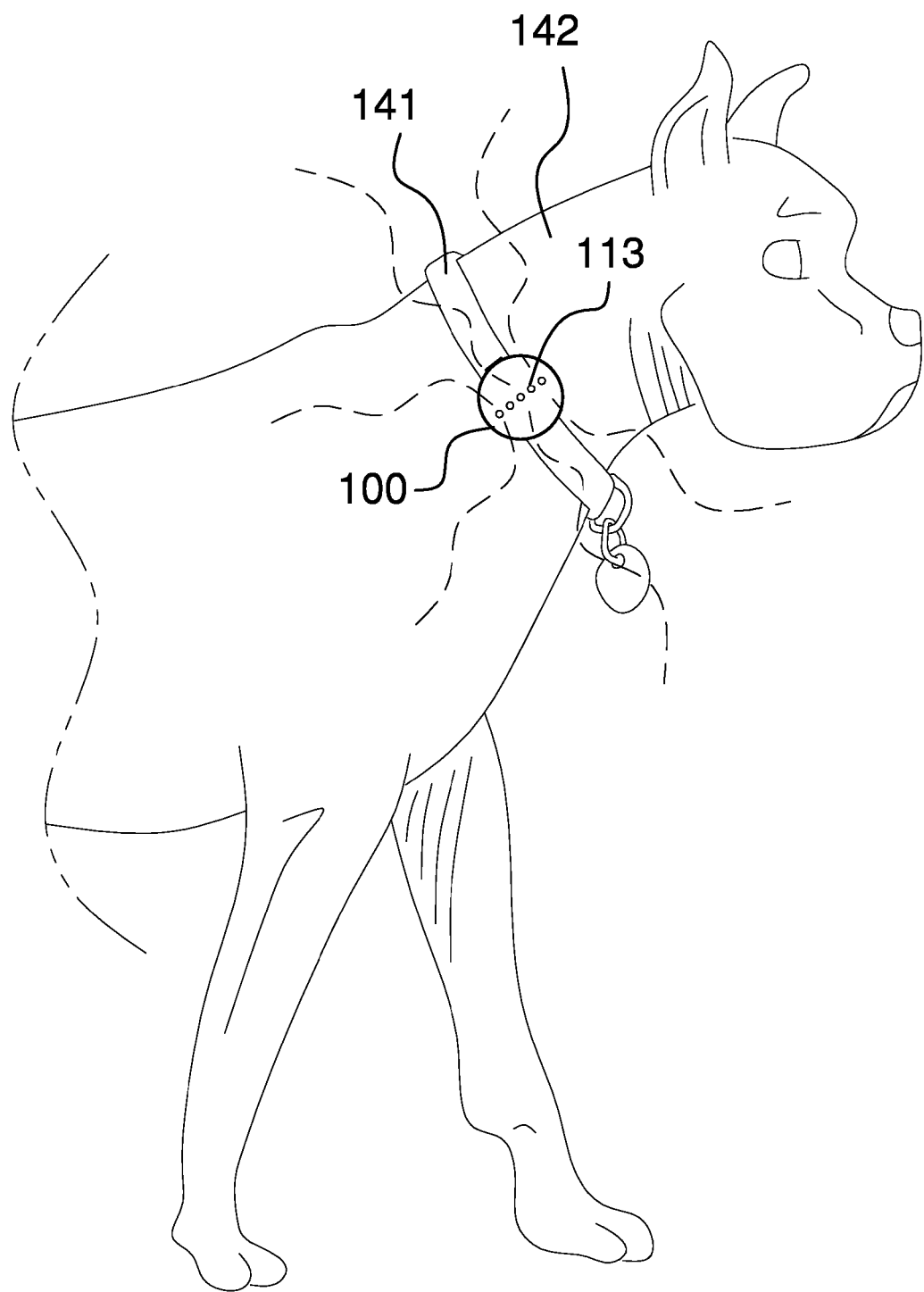
FIG. 5 is an in use view of an embodiment of the disclosure.

Detailed reference will now be made to one or more potential embodiments of the disclosure, which are illustrated in FIGS. 1 through 5.

The scent-dispensing animal collar accessory 100 (hereinafter invention) comprises a container 101, an attachment device 102, and a fragrance device 103. The invention 100 is adapted for use with a collar 141 that is worn by an animal 142. The invention 100 is a container 101 that is attached to the collar 141. The fragrance device 103 is stored within the container 101. The attachment device 102 is used to attach the container 101 to the collar 141. The fragrance device 103 is a chemical device that releases one or more aroma compounds. Air flow through the container 101 will disperse the one or more aroma compounds into the atmosphere in a manner that deemphasizes existing aromas that may be associated with the animal 142 or the collar 141.

The container 101 further comprises a receptacle 111, a lid 112, a plurality of holes 113, a hinge 114, and a latch 115. As shown most clearly in FIG. 1, the receptacle 111 is a capped tube. The inner diameter of the receptacle 111 is sized such that the receptacle 111 will receive the fragrance device 103. The fragrance device 103 is discussed elsewhere in this disclosure. The open end of the receptacle 111 is enclosed with the lid 112. The lid 112 is a disk shaped structure with an outer diameter that corresponds to the outer diameter of the receptacle 111. The lid 112 has formed in it a plurality of holes 113. The plurality of holes 113 is a collection of apertures that allow air to flow into and out of the receptacle 111.

The lid 112 is attached to the receptacle 111 using a hinge 114 such that the lid 112 can be rotated towards or away from the open base of the receptacle 111. When the lid 112 is in the closed position, meaning that access to the interior of the receptacle 111 is impeded, the lid 112 is held in the closed position with the latch 115. The latch 115 is a fastener attaches the lid 112 to the receptacle 111. Methods to attach lids 112 to receptacles 111 using hinges are well known and documented in the mechanical arts. Methods to secure lids 112 to receptacles 111 using latches are well known and documented in the mechanical arts. In the first potential embodiment of the disclosure, the latch 115 is a locking tab 116 arrangement. Locking tabs 116 are well known and documented in the mechanical arts and are discussed in detail elsewhere in this disclosure.

The attachment device 102 is used to attach the container 101 to the collar 141. As shown most clearly in FIG. 3, the attachment device 102 is a curved cantilever 121 that is further defined with a first end 151 and a second end 152. The first end 151 of the curved cantilever 121 is attached to the receptacle 111. The second end 152 of the curved cantilever 121 is free. The curved cantilever 121 acts as a spring. Specifically, when a force is applied perpendicularly to the surface of the curved cantilever 121, the elasticity of the curved cantilever 121 creates a rotational torque that opposes the displacement created by rotating the curved cantilever 121 around a pivot point located at the first end 151 where the curved cantilever 121 is attached to the receptacle 111. This rotational torque places a strain on the curved cantilever 121 such that the force of the strain is in the direction that returns the curved cantilever 121 to its original position.

When a collar 141 is inserted between the curved cantilever 121 and the receptacle 111, the spring like action of the curved cantilever 121 produces a clamping force that holds the invention 100 securely in position when the invention 100 is attached to a collar 141.

The fragrance device 103 comprises a petrolatum 131 and an essential oil 132. The essential oil 132 is dissolved into solution with the petrolatum 131. The concentration of the essential oil 132 is selected such that the fragrance device 103 forms a soft solid or gel like structure that can be manipulated with the hands. It is recommended that the petrolatum 131 be selected such that the melting point of the petrolatum 131 is greater than 40 C. The fragrance device 103 is formed into a disk shaped structure with dimensions such that the outer diameter of the fragrance device 103 is less than the inner diameter of the receptacle 111. Optionally, a base structure 133 can be placed within the fragrance device 103 to make the fragrance device 103 easier to handle.

A commercially available card stock cut into the form or a disk would be suitable for this purpose. A card stock with a weight greater than or equal to 210 gsm (for example a business card stock) is preferred. Essential oils suitable for use in the fragrance device 103 include, but are not limited to, basil oil, black pepper oil, caraway oil, *cannabis* flower oil, cedar wood oil, cinnamon oil, citronella oil, chamomile oil, clove oil, davana oil, *eucalyptus* oil, frankincense oil, horseradish oil, jasmine, oil, lavender oil, lemon oil, mandarin, nutmeg, orange oil, oregano oil, peppermint oil, pine oil, sandalwood oil, and star anise oil. Basil oil, citronella oil, clove oil, and peppermint oil are traditionally considered to have insect repellent properties.

To use the invention 100, a fragrance device 103 is selected and placed in the container 101 as described elsewhere in this disclosure. The attachment device 102 is then used to attach the invention 100 to the collar 141 of an animal 142.

In the first potential embodiment of the disclosure, the container 101 and the attachment device 102, as described in this disclosure, are formed as a single unit from molded plastic. Suitable plastics include, but are not limited to, polyethylene, polyvinylchloride, or polycarbonate.

The following definitions were used in this disclosure:

Cantilever: As used in this disclosure, a cantilever is a beam or other structure that projects away from an object and is supported on only one end.

Capped Tube: As used in this disclosure, a capped tube is a tube with one closed end and one open end.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; or, 4) the point, pivot, or axis around which something revolves.

Center Axis: As used in this disclosure, the center axis is the axis of a cylinder or cone like structure. When the center axes of two cylinder or like structures share the same line they are said to be aligned. When the center axes of two cylinder like structures do not share the same line they are said to be offset.

Correspond: As used in this disclosure, the term correspond is used as a comparison between two or more objects wherein one or more properties shared by the two or more objects match, agree, or align within acceptable manufacturing tolerances.

Cylinder: As used in this disclosure, a cylinder is a geometric structure defined by two identical flat and parallel bases, also commonly referred to as ends, which are circular in shape and connected with a single curved surface wherein when the cross section of the cylinder remains the same from one end to another. The axis of the cylinder is formed by the straight line that connects the center of each of the two identical flat and parallel ends of the cylinder. In this disclosure, the term cylinder specifically means a right cylinder, which is defined as a cylinder wherein the curved surface perpendicularly intersects with the two identical flat and parallel ends.

Diameter: As used in this disclosure, a diameter of an object is a straight line segment that passes through the center of an object. The line segment of the diameter is terminated at the perimeter or boundary of the object through which the line segment of the diameter runs.

Disk: As used in this disclosure, a disk is a cylindrically shaped object that is flat in appearance.

Fastener: As used in this disclosure, a fastener is a device that is used to loin or affix two objects. Fasteners generally comprise a first element, which is attached to the first object and second element which is attached to the second object such that the first element and the second element join to affix the first object and the second object.

Gel: As used in this disclosure, a gel is a substance comprising mostly of liquid (by mass) that is trapped in a cross-linked network of proteins and peptides that exhibits the properties of a solid.

GSM: As used in this disclosure, GSM is an acronym that stands for grams per square meter. The gsm is a standardized measure of the grammage of paper weight that is defined in ISO 536. The gsm is essentially the weight of an AO (as defined in ISO 236) size sheet of paper in grams. The dimensions of AO size paper is 210 mm×297 mm.

Hinge: As used in this disclosure, a hinge is a device that permits the turning, rotating, or pivoting of a first object relative to a second object.

Inner Diameter: As used in this disclosure, the term inner diameter is used in the same way that a plumber would refer to the inner diameter of a pipe.

Locking Tab: As used in this disclosure, a locking tab is a two element fastener wherein the first element of the fastener, which is mounted on a first object is a cantilever spring and the second element of the fastener is a hole which is formed in a second object. The free end of the cantilever spring has a hook formed in it such that when the free end of the cantilever spring is inserted into the hole, the hook latches against the edge of the hole preventing inadvertent removal of the cantilever spring. The first element is removed from the second element by bending the cantilever spring such that the hook clears the edge of the hole and then pulling the first element away from the second element.

Outer Diameter: As used in this disclosure, the term outer diameter is used in the same way that a plumber would refer to the outer diameter of a pipe.

Paraffin: As used in this disclosure, paraffin is an alkane with a carbon base chain of between 20 and 40 atoms that is solid at room temperature.

Perimeter: As used in this disclosure, a perimeter is one or more curved or straight lines that bounds an enclosed area on a plane or surface. The perimeter of a circle is commonly referred to as a circumference.

Petrolatum: As used in this disclosure, petrolatum is a paraffin with a carbon base chain of greater than 25 atoms. Petrolatum is generally in a semi-solid or gel like state at room temperatures. Petroleum jellies are a common example of a petrolatum.

Pivot: As used in this disclosure, a pivot is a rod or shaft around which an object rotates or swings.

Tube: As used in this disclosure, a tube is a hollow cylindrical device that is used for transporting liquids and gasses. The line that connects the center of the first base of the cylinder to the center of the second base of the cylinder is referred to as the axis of the cylinder or the centerline of the tube.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A deodorizer comprising:
a container, an attachment device, and a fragrance device;
wherein the deodorizer is adapted for use with a collar that is worn by an animal;
wherein the container is attached to the collar using the attachment device;
wherein the fragrance device is stored within the container;
wherein the fragrance device is a chemical device that releases one or more aroma compounds;
wherein air flow through the container will disperse the one or more aroma compounds into the atmosphere;
wherein the container further comprises a receptacle, a lid, a hinge, and a latch;
wherein the hinge attaches the lid to the receptacle;
wherein the latch secures the lid to the receptacle;
wherein the receptacle is a capped tube;
wherein the open end of the receptacle is enclosed with the lid;
wherein the lid is a disk shaped structure with an outer diameter that corresponds to the outer diameter of the receptacle;
wherein the lid is attached to the receptacle using the hinge such that the lid can be rotated towards or away from the open base of the receptacle using the hinge as a pivot;
wherein the lid further comprises a plurality of holes;
wherein the plurality of holes is a collection of apertures that allow air to flow into and out of the receptacle;
wherein the latch is a fastener;
wherein the attachment device is a curved cantilever;
wherein the curved cantilever is further defined with a first end and a second end;
wherein the first end of the curved cantilever is attached to the receptacle;
wherein the curved cantilever is a spring;
wherein when the collar is inserted between the curved cantilever and the receptacle, the spring action of the curved cantilever produces a clamping force that holds the deodorizer to the collar;
wherein the fragrance device comprises a petrolatum and an essential oil;
wherein the essential oil is dissolved into solution with the petrolatum;
wherein the fragrance device forms a structure selected from the group consisting of a solid structure or a gel structure;
wherein the fragrance device is formed into a disk shaped structure with dimensions such that the outer diameter of the fragrance device is less than the inner diameter of the receptacle;
wherein the fragrance device further comprises a base structure;
wherein the base structure is placed within the essential oil and petrolatum solution;
wherein the base structure is formed from a card stock;
wherein the card stock has a minimum weight of 200 gsm.

2. The deodorizer according to claim 1 wherein the melting point of the petrolatum is greater than or equal to 40 C.

3. The deodorizer according to claim 2 wherein the essential oil is selected from the group consisting of basil oil, black pepper oil, caraway oil, *cannabis* flower oil, cedar wood oil, cinnamon oil, citronella oil, chamomile oil, clove oil, davana oil, *eucalyptus* oil, frankincense oil, horseradish oil, jasmine oil, lavender oil, lemon oil, mandarin, nutmeg, orange oil, oregano oil, peppermint oil, pine oil, sandalwood oil, or star anise oil.

4. The deodorizer according to claim 1
wherein the fragrance device comprises a petrolatum and an essential oil;
wherein the essential oil is dissolved into solution with the petrolatum;
wherein the fragrance device forms a structure selected from the group consisting of a solid structure or a gel structure.

5. The deodorizer according to claim 4
wherein the open end of the receptacle is enclosed with the lid;

wherein the lid is a disk shaped structure with an outer diameter that corresponds to the outer diameter of the receptacle;

wherein the lid is attached to the receptacle using a hinge such that the lid can be rotated towards or away from the open base of the receptacle using the hinge as a pivot;

wherein the lid further comprises a plurality of holes;

wherein the plurality of holes is a collection of apertures that allow air to flow into and out of the receptacle.

6. The deodorizer according to claim 5 wherein the attachment device is a curved cantilever;

wherein the curved cantilever is further defined with a first end and a second end;

wherein the first end of the curved cantilever is attached to the receptacle;

wherein the curved cantilever is a spring;

wherein when the collar is inserted between the curved cantilever and the receptacle, the spring action of the curved cantilever produces a clamping force that holds the deodorizer to the collar.

7. The deodorizer according to claim 6 wherein the fragrance device further comprises a base structure;

wherein the base structure is placed within the essential oil and petrolatum solution;

wherein the base structure is formed from a card stock;

wherein the card stock has a minimum weight of 200 gsm.

8. The deodorizer according to claim 6 wherein the melting point of the petrolatum is greater than or equal to 40 C.

9. The deodorizer according to claim 6 wherein the essential oil is selected from the group consisting of basil oil, black pepper oil, caraway oil, *cannabis* flower oil, cedar wood oil, cinnamon oil, citronella oil, chamomile oil, clove oil, davana oil, *eucalyptus* oil, frankincense oil, horseradish oil, jasmine oil, lavender oil, lemon oil, mandarin, nutmeg, orange oil, oregano oil, peppermint oil, pine oil, sandalwood oil, or star anise oil.

\* \* \* \* \*